(12) United States Patent
Le et al.

(10) Patent No.: US 12,080,021 B2
(45) Date of Patent: Sep. 3, 2024

(54) TRAINING A MACHINE LEARNING ALGORITHM USING DIGITALLY RECONSTRUCTED RADIOGRAPHS

(71) Applicant: Brainlab AG, Munich (DE)

(72) Inventors: Kim Le, Munich (DE); Yannic Meurer, Laim (DE); Thomas Drexl, Poing (DE); Thomas Feilkas, Kirchseeon (DE)

(73) Assignee: BRAINLAB AG, Munich (DE)

( * ) Notice: Subject to any disclaimer, the term of this patent is extended or adjusted under 35 U.S.C. 154(b) by 748 days.

(21) Appl. No.: 17/274,580

(22) PCT Filed: Sep. 20, 2019

(86) PCT No.: PCT/EP2019/000277
§ 371 (c)(1),
(2) Date: Mar. 9, 2021

(87) PCT Pub. No.: WO2021/052552
PCT Pub. Date: Mar. 25, 2021

(65) Prior Publication Data
US 2021/0383565 A1   Dec. 9, 2021

(51) Int. Cl.
*G06T 7/73* (2017.01)
*G06N 3/04* (2023.01)
(Continued)

(52) U.S. Cl.
CPC ............... *G06T 7/73* (2017.01); *G06N 3/04* (2013.01); *G06N 3/08* (2013.01); *G06T 7/0012* (2013.01);
(Continued)

(58) Field of Classification Search
CPC .............................. G06T 7/73; A61B 17/1703
(Continued)

(56) References Cited

U.S. PATENT DOCUMENTS 8,121,362 B2   2/2012   Zhan et al.
8,620,040 B2   12/2013  Grosskopf
(Continued)

FOREIGN PATENT DOCUMENTS

BR   112013001487   1/2017
CN      103220974   7/2013
(Continued)

OTHER PUBLICATIONS

Litjens et al., "A Survey On Deep Learning in Medical Image Analysis" Diagnostic Image Analysis Group, Radboud University Medical Center, Nijmegen, The Netherlands. Elsevier. Dated Jul. 26, 2017.
(Continued)

*Primary Examiner* — Ruay Ho
(74) *Attorney, Agent, or Firm* — Gray Ice Higdon (57) ABSTRACT

Disclosed is a computer-implemented method of training a likelihood-based computational model for determining the position of an image representation of an annotated anatomical structure in a two-dimensional x-ray image, wherein the method encompasses inputting medical DRRs together with annotation to a machine learning algorithm to train the algorithm, i.e. to generate adapted learnable parameters of the machine learning model. The annotations may be derived from metadata associated with the DRRs or may be included in atlas data which is matched with the DRRs to establish a relation between the annotations included in the atlas data and the DRRs. The thus generated machine learning algorithm may then be used to analyse clinical or synthesized DRRs so as to appropriately add annotations to those DRRs and/or identify the position of an anatomical structure in those DRRs.

13 Claims, 5 Drawing Sheets

(51) Int. Cl.
  *G06N 3/08*   (2023.01)
  *G06T 7/00*   (2017.01)
  *G16H 30/20*  (2018.01)
  *G16H 30/40*  (2018.01)
  *G16H 50/20*  (2018.01)

(52) U.S. Cl.
  CPC ............ *G16H 30/20* (2018.01); *G16H 30/40* (2018.01); *G16H 50/20* (2018.01); *G06T 2207/10121* (2013.01); *G06T 2207/20081* (2013.01); *G06T 2207/20084* (2013.01); *G06T 2207/30004* (2013.01)

(58) Field of Classification Search
  USPC .............................................. 706/12; 382/128
  See application file for complete search history.

(56) References Cited

U.S. PATENT DOCUMENTS

| | | | |
|---|---|---|---|
| 8,666,128 B2 * | 3/2014 | Chaney | G06T 7/344 |
| | | | 382/128 |
| 8,774,482 B2 | 7/2014 | Reisman et al. | |
| 9,014,485 B2 | 4/2015 | Moehrle | |
| 9,595,120 B2 | 3/2017 | Nguyen et al. | |
| 9,764,162 B1 * | 9/2017 | Willcut | G06T 7/0014 |
| 10,282,588 B2 | 5/2019 | Comaniciu et al. | |
| 10,282,840 B2 | 5/2019 | Moehrle et al. | |
| 10,929,989 B2 * | 2/2021 | Kurzendorfer | G06T 7/30 |
| 2008/0267483 A1 | 10/2008 | Zhan et al. | |
| 2010/0166283 A1 | 7/2010 | Grosskopf | |
| 2011/0286649 A1 | 11/2011 | Reisman et al. | |
| 2012/0020536 A1 | 1/2012 | Moehrle | |
| 2014/0219500 A1 | 8/2014 | Moehrle | |
| 2016/0314600 A1 | 10/2016 | Nguyen et al. | |
| 2017/0357844 A1 | 12/2017 | Comaniciu et al. | |
| 2018/0061058 A1 | 3/2018 | Xu et al. | |
| 2018/0315182 A1 | 11/2018 | Rapaka et al. | |
| 2019/0030371 A1 | 1/2019 | Han | |
| 2019/0046813 A1 * | 2/2019 | Zhou | A61N 5/10 |
| 2019/0050999 A1 * | 2/2019 | Piat | G06T 7/337 |
| 2019/0220978 A1 | 7/2019 | Moehrle et al. | |
| 2019/0251694 A1 * | 8/2019 | Han | G06T 7/174 |
| 2020/0129780 A1 * | 4/2020 | Lachaine | G16H 20/40 |
| 2020/0129784 A1 * | 4/2020 | Bériault | G06N 3/08 |
| 2021/0304402 A1 * | 9/2021 | Morgas | G06T 7/12 |

FOREIGN PATENT DOCUMENTS

| | | | |
|---|---|---|---|
| CN | 107403058 | 11/2017 | |
| CN | 107492090 | 12/2017 | |
| CN | 108784655 | 11/2018 | |
| DE | 102009006636 A1 | 7/2010 | |
| DE | 102009006636 B4 | 2/2016 | |
| EP | 3404666 A2 | 11/2018 | |
| EP | 3404666 A3 | 1/2019 | |
| WO | 2008136966 A2 | 11/2008 | |
| WO | 2008136966 A3 | 4/2009 | |
| WO | 2012012664 A2 | 1/2012 | |
| WO | 2012012664 A3 | 4/2012 | |
| WO | 2019003434 | 1/2019 | |
| WO | 2019003474 | 1/2019 | |
| WO | WO-2020163358 A1 * | 8/2020 | ......... A61B 17/1703 |

OTHER PUBLICATIONS

International Search Report and Written Opinion issued for Application No. PCT/EP2019/000277 dated Jun. 4, 2020.

Shotton et al., "Efficient Human Pose Estimation from Single Depth Images" TRANS.PAMI. pp. 175-192. 2012.

Criminisi et al., "Decision Forests for Computer Vision and Medical Image Analysis" Advances in Computer Vision and Pattern Recognition, DOI 10.1007/978-1-4471-4929-3_1. Springer-Verlag London. 2013.

Mathias Unberath et al., "Enabling Machine Learning in X-Ray-Based Procedures Via Realistic Simulation of Image Formation", International Journal of Computer Assisted Radiology and Surgery, Springer, Germany, Published Online Jun. 11, 2019; vol. 14 No. 9, pp. 1517-1528; 12 pages; https://doi.org/10.1007/s11548-019-02011-2.

Mathias Unberath et al., "DeepDRR—A Catalyst for Machine Learning in Fluoroscopy-Guided Procedures", Advances in Biometrics: International Conference, ICB 2007, Seoul, Korea, Aug. 27-29, 2007; Lecture Notes in Computer Science, Springer, Berlin, Heidelberg, pp. 98-106; 9 pages.

Zhao We et al., "Incorporating Imaging Information From Deep Neural Network Layers Into Image Guided Radiation Therapy (IGRT)", Radiotherapy and Oncology, Elsevier, Ireland, vol. 140, dated Jul. 11, 2019, pp. 167-174; 8 pages.

* cited by examiner

TRAINING A MACHINE LEARNING ALGORITHM USING DIGITALLY RECONSTRUCTED RADIOGRAPHS

FIELD OF THE INVENTION

The present invention relates to a computer-implemented method of training a likelihood-based computational model for determining the position of an image representation of an annotated anatomical structure in a two-dimensional x-ray image, a corresponding computer program, a computer-implemented method of determining a relation between an anatomical structure represented in a two-dimensional medical image and an annotation for the anatomical structure, a program storage medium storing such a program and a computer for executing the program, as well as a medical system comprising an electronic data storage device and the aforementioned computer.

TECHNICAL BACKGROUND

Training of machine learning algorithms using synthetic models has been used before. For example, the Microsoft Kinect was trained on 3D models which provided the labels per pose.

The literature does not mention using digitally reconstructed radiographs (DRRs) for training algorithms which are then used together with other datasets. Training only on clinical data is difficult as gathering data may take a lot of time, the data may be of low quality and has to be sorted and labeled for machine learning. Using DRRs, the labeling process can be automated.

The present invention has the object of providing an improved method of training and using an artificial intelligence (AI) algorithm for applying annotations to medical image data or detecting an image position of a predetermined anatomical structure in medical image data.

The present invention can be used image-guided procedures e.g. in connection with a system for radiotherapy such as VERO® and ExacTrac®, or surgical navigation such as Curve® or Kick®, or cloud-based surgical planning such as Quentry®, all products of Brainlab AG.

Aspects of the present invention, examples and exemplary steps and their embodiments are disclosed in the following. Different exemplary features of the invention can be combined in accordance with the invention wherever technically expedient and feasible.

Exemplary Short Description of the Invention

In the following, a short description of the specific features of the present invention is given which shall not be understood to limit the invention only to the features or a combination of the features described in this section.

The disclosed method encompasses inputting medical DRRs together with annotation to a machine learning algorithm to train the algorithm, i.e. to generate adapted learnable parameters of the machine learning model. The annotations may be derived from metadata associated with the DRRs or may be included in atlas data which is matched with the DRRs to establish a relation between the annotations included in the atlas data and the DRRs. The thus generated machine learning algorithm may then be used to analyse clinical or synthesized DRRs so as to appropriately add annotations to those DRRs and/or identify the position of an anatomical structure in those DRRs.

General Description of the Invention

In this section, a description of the general features of the present invention is given for example by referring to possible embodiments of the invention.

In general, the invention reaches the aforementioned object by providing, in a first aspect, a computer-implemented medical method of training a likelihood-based computational model for determining the position of an image representation of an annotated anatomical structure in a two-dimensional x-ray image. The method according to the first aspect comprises executing, on at least one processor of at least one computer (for example at least one computer being part of a navigation system), the following exemplary steps which are executed by the at least one processor.

In a (for example first) exemplary step of the method according to the first aspect, image training data is acquired which describes synthesized two-dimensional x-ray images (for example, digitally reconstructed radiographs—DRRs), also called training images, including an image representation of the anatomical structure. This step corresponds to inputting a set of training DRRs used for training the likelihood—based computational model. The term of anatomical structure encompasses an anomaly such as pathological tissue such as a tumour or fractures/broken bones or shifted bones or medical implants like a screw or an artificial disc or limb.

In a (for example second) exemplary step of the method according to the first aspect, annotation data is acquired which describes an annotation for the anatomical structure. The annotation is for example at least one of information describing a perspective onto the anatomical structure defining the image representation of the anatomical structure (such as information describing whether the image representation was generated from a left or a right side of the anatomical structure), information describing a subset or a segmentation of the image representation (such as a bounding box delimiting the subset) or information describing a classification defining a property of the anatomical structure (such as a degree of pathology of the anatomical structure or its identity for example its anatomical designation and/or name). For example, the annotation data is determined from metadata included in the image training data. In one example, atlas data is acquired which describes an image-based model of the anatomical structure, and the annotation data is then determined for example based on the image training data and the atlas data. This is for example done by matching the training images with the image-based model, for example by executing an image fusion algorithm on the two data sets to find corresponding image structures. The image-based model for example comprises data objects such as representations of anatomical landmarks, the geometry of which can be matched with image constituents of the training images to find structures in the image-based model which correspond to certain structures visible in the training images. The annotation may be defined in relation to the corresponding structure in the image-based model and transferred to the training images based on the matching.

In a (for example third) exemplary step of the method according to the first aspect, model parameter data is determined which describes model parameters (e.g. learnable parameters such as biases, batch normalization or weights) of a likelihood-based computational model for establishing a likelihood-based relation (e.g. a likelihood-based association) between the anatomical structure in the two-dimensional x-ray images and the annotation. For example, the computational model comprises or consists of an artificial intelligence (AI) algorithm, for example a machine learning (ML) algorithm; in one example, a convolutional neural network is part of the computational model. The model parameter data is determined for example by inputting the image training data and the annotation data into a function which establishes the likelihood-based relation (and then executing the function on the basis of this input). For example, the function establishes a likelihood-based relation between a position of the anatomical structure in the two-dimensional x-ray images and a position for displaying the annotation in the two-dimensional x-ray images. Thereby, the computational model such as a machine learning algorithm can be trained to establish a relation between a position of a landmark and a position for labelling it in association with the training image, e.g. in the image.

In an example of the method according to the first aspect, medical image data is acquired which describes three-dimensional medical images including an image representation of the anatomical structure, wherein the training image data is determined by determining an image value threshold (such as intensity threshold) associated with the image representation of the anatomical structure in the three-dimensional medical images and defining a corresponding intensity mapping function and generating the image representation of the anatomical structure in each of the two-dimensional synthesized x-ray images from the image representation of the anatomical structure in at least one, e.g. exactly one, a real subset or all, of the three-dimensional medical images based on the intensity mapping function.

In an example of the method according to the first aspect, atlas data is acquired which describes an image-based model of the anatomical structure and at least one projection parameter for generating the two-dimensional medical images. Then, the two-dimensional medical images are generated based on the at least one projection parameter. Specifically, the projection parameters such as the perspective for generating the training images (the DRRs) are taken from the atlas data.

In a second aspect, the invention is directed to a computer-implemented method of determining a relation between an anatomical structure represented in a two-dimensional medical image and an annotation for the anatomical structure. The method according to the second aspect comprises executing, on at least one processor of at least one computer (for example at least one computer being part of a navigation system), the following exemplary steps which are executed by the at least one processor.

In a (for example first) exemplary step of the method according to the second aspect, patient image data is acquired which describes a (synthetic or clinical, i.e. real) two-dimensional x-ray image including an image representation of an anatomical structure of a patient. For example, the patient image data has been generated by synthesizing the two-dimensional x-ray image from a three-dimensional image of the anatomical structure, or wherein the patient image data has been generated by applying an x-ray-based imaging modality such as a fluoroscopic imaging modality or a tomographic imaging modality such as computed x-ray tomography imaging or magnetic resonance imaging to the anatomical structure (and, in the latter case, by generating the two-dimensional x-ray image from the computed x-ray tomography or magnetic resonance tomography, respectively).

In a (for example second) exemplary step of the method according to the second aspect, structure annotation prediction data is determined which describes, according to a certain likelihood determined by the computational model, a position of the image representation of the anatomical structure in the two-dimensional x-ray image described by the patient image data and an annotation for the anatomical structure, wherein the structure annotation data is determined by inputting the patient image data into a function which establishes a likelihood-based relation between the image representation of the anatomical structure in the two-dimensional x-ray image and the annotation for the anatomical structure, the function being part of a computational model which has been trained by executing the method according to the first aspect (and then executing the function on the basis of this input)

In an example of the method according to the second aspect, the function establishes a likelihood-based relation between a position of the anatomical structure in the two-dimensional x-ray images described by the patient image data and a position for displaying the annotation in the two-dimensional x-ray images described by the patient image data, and the structure annotation data describes a likelihood-based relation (e.g. a likelihood-based association) between the position of the image representation of the anatomical structure in the two-dimensional x-ray image described by the patient image data and a position for displaying the annotation for the anatomical structure in the two-dimensional x-ray image described by the patient image data.

In a third aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first or second aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first or second aspect. The signal wave is in one example a data carrier signal carrying the aforementioned computer program. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the thirds aspect therefore may alternatively or additionally relate to a data stream representative of the aforementioned program.

In a fourth aspect, the invention is directed to a computer-readable program storage medium on which the program according to the third aspect is stored. The program storage medium is for example non-transitory.

In a fifth aspect, the invention is directed to a program storage medium on which data defining the model parameters and the architecture of a likelihood-based computational model which has been trained by executing the method according to the first aspect is stored.

In a sixth aspect, the invention is directed to a data carrier signal carrying data defining the model parameters and the architecture of a likelihood-based computational model which has been trained by executing the method according to the first aspect, and/or a data stream which carries data defining the model parameters and the architecture of a likelihood-based computational model which has been trained by executing the method according to the first aspect.

In a seventh aspect, the invention is directed to at least one computer (for example, a computer), comprising at least one processor (for example, a processor) and at least one memory (for example, a memory), wherein the program according to the third aspect is running on the processor or is loaded into the memory, or wherein the at least one computer comprises the computer-readable program storage medium according to the fourth aspect.

In an eighth aspect, the invention is directed to a system for determining a relation between an anatomical structure represented in a two-dimensional medical image and an annotation for the anatomical structure, comprising:
  a) the at least one computer according to the preceding claim;
  b) at least one electronic data storage device storing the patient image data;
  c) the program storage medium according to the preceding claim; and
  wherein the at least one computer is operably coupled to
    the at least one electronic data storage device for acquiring, from the at least one electronic data storage device, the patient image data, and for storing, in the at least one electronic data storage device, at least the structure annotation prediction data; and
    the program storage medium for acquiring, from the program storage medium, the data defining the model parameters and the architecture of the likelihood-based computational model.

Alternatively or additionally, the invention according to the fifth aspect is directed to a for example non-transitory computer-readable program storage medium storing a program for causing the computer according to the fourth aspect to execute the data processing steps of the method according to the first or second aspect.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of applying ionizing radiation to a patient's body, for example to generate the patient image data. Rather, the patient image data has already been generated before execution of the inventive method according to the second aspect ensues. For this reason alone, no surgical or therapeutic activity and in particular no surgical or therapeutic step is necessitated or implied by carrying out the invention. More particularly, the invention does not involve or in particular comprise or encompass any surgical or therapeutic activity. The invention is instead directed as applicable to processing medical image data.

The present invention also relates to the use of the system according to the eighth aspect or the computer according to the seventh aspect for training a likelihood-based computational model for determining the position of an image representation of an annotated anatomical structure in a two-dimensional x-ray image or determining a relation between an anatomical structure represented in a two-dimensional medical image and an annotation for the anatomical structure, respectively, by executing the method according to the first or second aspect, respectively.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

The movements of the treatment body parts are for example due to movements which are referred to in the following as "vital movements". Reference is also made in this respect to EP 2 189 943 A1 and EP 2 189 940 A1, also published as US 2010/0125195 A1 and US 2010/0160836 A1, respectively, which discuss these vital movements in detail. In order to determine the position of the treatment body parts, analytical devices such as x-ray devices, CT devices or MRT devices are used to generate analytical images (such as x-ray images or MRT images) of the body. For example, analytical devices are constituted to perform medical imaging methods. Analytical devices for example use medical imaging methods and are for example devices for analysing a patient's body, for instance by using waves and/or radiation and/or energy beams, for example electromagnetic waves and/or radiation, ultrasound waves and/or particles beams. Analytical devices are for example devices which generate images (for example, two-dimensional or three-dimensional images) of the patient's body (and for example of internal structures and/or anatomical parts of the patient's body) by analysing the body. Analytical devices are for example used in medical diagnosis, for example in radiology. However, it can be difficult to identify the treatment body part within the analytical image. It can for example be easier to identify an indicator body part which correlates with changes in the position of the treatment body part and for example the movement of the treatment body part. Tracking an indicator body part thus allows a movement of the treatment body part to be tracked on the basis of a known correlation between the changes in the position (for example the movements) of the indicator body part and the changes in the position (for example the movements) of the treatment body part. As an alternative to or in addition to tracking indicator body parts, marker devices (which can be used as an indicator and thus referred to as "marker indicators") can be tracked using marker detection devices. The position of the marker indicators has a known (predetermined) correlation with (for example, a fixed relative position relative to) the position of indicator structures (such as the thoracic wall, for example true ribs or false ribs, or the diaphragm or intestinal walls, etc.) which for example change their position due to vital movements.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of such an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
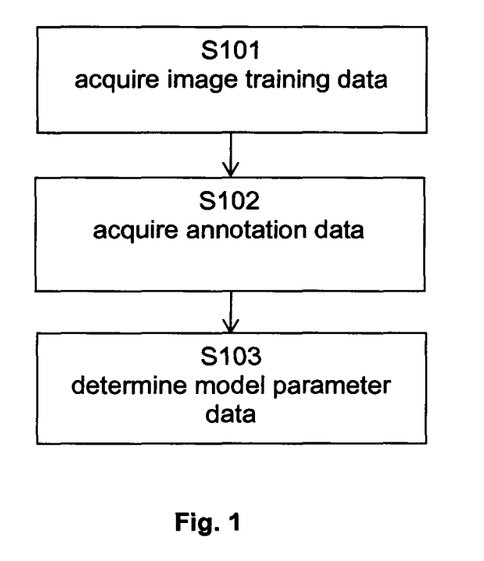
FIG. 1 illustrates a basic flow of the method according to the first aspect.

FIG. 1 illustrates the basic steps of the method according to the first aspect, in which step S101 encompasses acquiring the image training data, step S102 encompasses acquiring the annotation data and subsequent step S103 encompasses determining the model parameter data.

Figure 2:
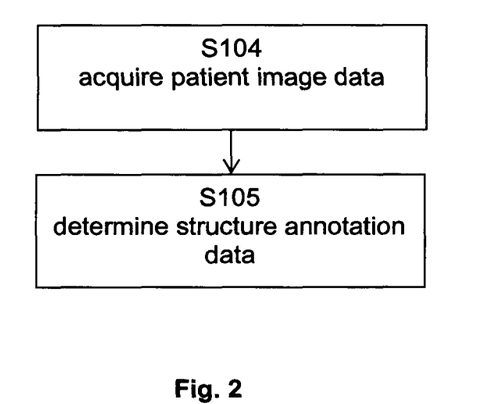
FIG. 2 illustrates a basic flow of the method according to the second aspect.

FIG. 2 describes the basic steps of the method according to the second aspect, in which step S104 encompasses acquiring the patient image data and step S105 encompasses determining the structure annotation data.

Figure 3:
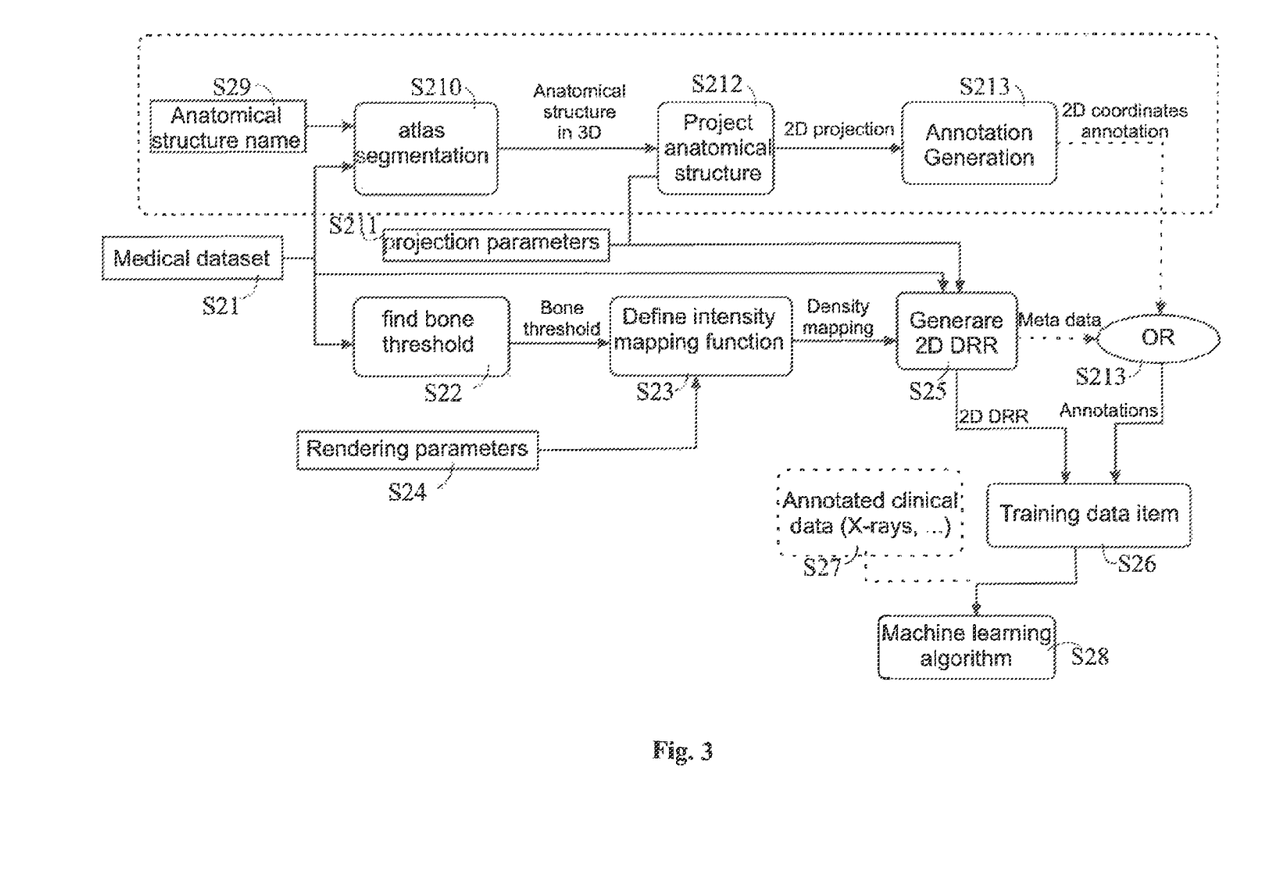
FIG. 3 shows an example of the method according to the first aspect.

FIG. 3 illustrates an example of the method according to the first aspect. In step S21, the patient image data embodied by a medical dataset is read, and an intensity threshold to identify a threshold for a greyscale representation (such as a predetermined Hounsfield unit value) for rendering bony tissue is found in subsequent step S22. On the basis of this threshold, step S23 carries on with defining an intensity mapping function, including rendering parameters read in step S24. The density/intensity mapping is then used in step S25 to generate two-dimensional DRRs from the medical data set. The DRRs are then used, together with annotations (i.e. at least one annotation), in step S26 to form the basis for a training data item usable for training a machine learning algorithm in step S28. Additionally, annotated clinical data such as real fluoroscopies may be optionally read in step S27 and used as basis in training the machine learning algorithm. The annotations to the DRRs may be read from metadata associated with the medical dataset or may be generated by using atlas data. To that end, step S29 may read an identifier such as the name of the relevant anatomical structure and use it for running a segmentation of the medical dataset based on atlas data. Additionally, the atlas data may store projection parameters for generating the DRRs which may be extracted in step S211 and the input to step S25. The segmented anatomical structure is projected from three-dimensions into two dimensions in step S212, and the two-dimensional projection is used for generating an annotation in step S213 which may be associated with the DRR generated in step S25 by using two-dimensional coordinates associated with the annotation.

Figure 4:
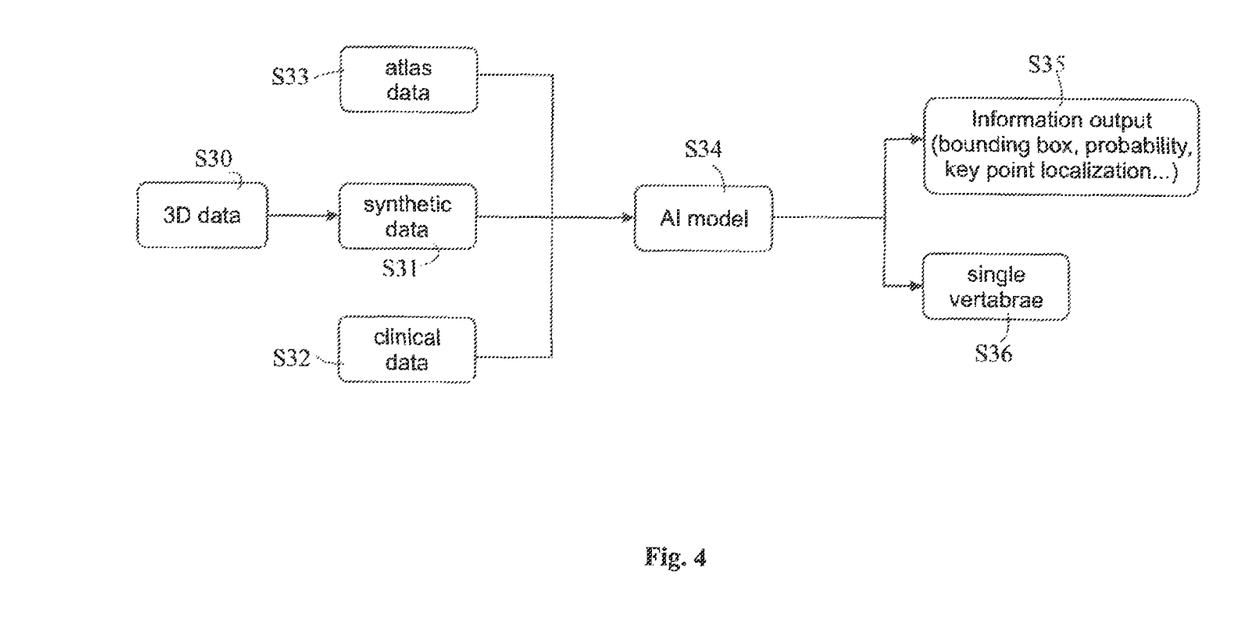
FIG. 4 shows the principle of using the example of FIG. 3.

FIG. 4 illustrates how three-dimensional data representing the patient image data is read in step S30 and used as an input for generating synthetic data in step S31 which may then be combined with atlas data read in step S33 and clinical data read in step S32 as input to a trained AI model which is then run in step S34 on that input to generate in step S35 information output (such as bounding box, a probability for an image constituent representing a certain anatomical structure or a key point or landmark localization, or determine for example the image position of predetermined anatomical structures such as single vertebrae in step S36.

Figure 5:
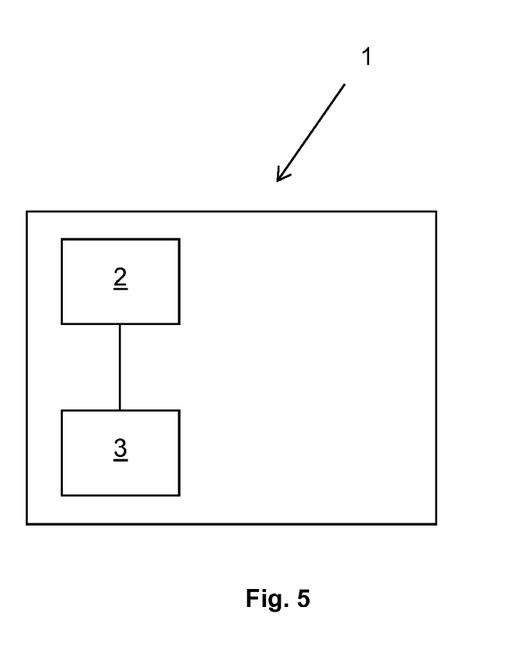
FIG. 5 is a schematic illustration of the system according to the fifth aspect.

FIG. 5 is a schematic illustration of the medical system 1 according to the eighth aspect. The system is in its entirety identified by reference sign 1 and comprises a computer 2, an electronic data storage device (such as a hard disc) 3 for storing at least the patient image data and. The components of the medical system 1 have the functionalities and properties explained above with regard to the eighth aspect of this disclosure.

A focus of the disclosed method according to the first aspect is to train a machine learning algorithm to detect objects and/or features in patient image data (such 3D data, e.g. CT or MRI, or 2D data such as x-ray images or fluoroscopies). The training is optimized using digital reconstructed radiographs in addition to real patient data as this allows to better fine tune the input data.

The benefit of using DRRs is the possibility to generate a large set of images, the image quality and content of which can be influenced. DRRs can be generated from CT datasets which means the algorithm can be used for both 3D datasets and for 2D images. By adjusting the bone threshold (which is detect automatically by applying a known method), the content of the output images can be adjusted to show, for example, only bone structures and no soft tissue. The projection parameters can be defined freely allowing to generate images from various shot directions which would be difficult to achieve in a clinical setting (and may not be possible at all due to ethical concerns/radiation doses/availability of clinical specimens).

In the following, an explanation of convolutional neural networks as an example of the machine learning algorithm to be used with the disclosed invention is provided with reference to FIGS. 6 to 10.

Convolutional networks, also known as convolutional neural networks, or CNNs, are an example of neural networks for processing data that has a known grid-like topology. Examples include time-series data, which can be thought of as a 1-D grid taking samples at regular time intervals, and image data, which can be thought of as a 2-D grid of pixels. The name "convolutional neural network" indicates that the network employs the mathematical operation of convolution. Convolution is a linear operation. Convolutional networks are simply neural networks that use convolution in place of general matrix multiplication in at least one of their layers. There are several variants on the convolution function that are widely used in practice for neural networks. In general, the operation used in a convolutional neural network does not correspond precisely to the definition of convolution as used in other fields, such as engineering or pure mathematics.

Figure 6:
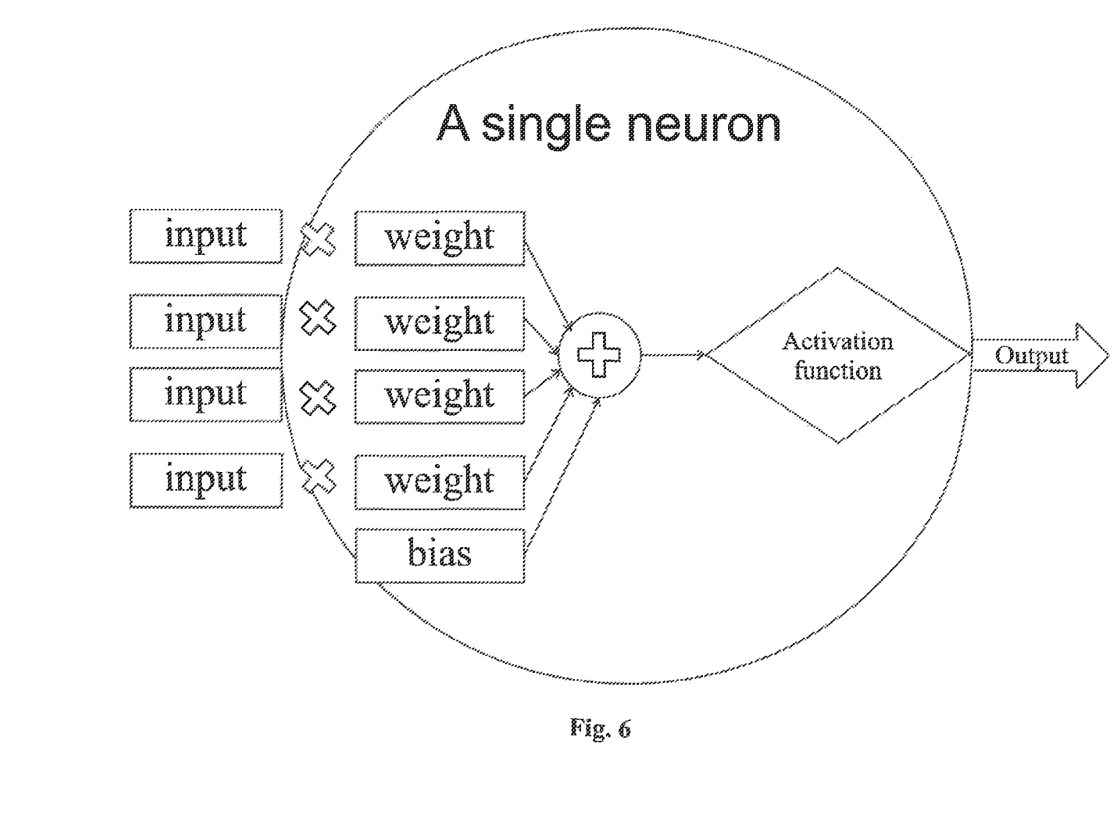
FIG. 6 shows the structure of a single neuron of a convolutional neural network.

The main component of convolutional neural networks are artificial neurons. FIG. 6 is an example of a single neuron depicted. The node in the middle represents a neuron, which takes all inputs $(x_i, \ldots, x_n)$ and multiplies them with their specific weights $(w_1, \ldots, w_n)$. The importance of the input is depending on the value of its weight. The addition of these computed values is called weighted sum which will be inserted into a activation function. The weighted sum z is defined as:

$$z = \sum_{i=0}^{m} x_i \cdot w_i \quad (1)$$

The bias b is an input-independant value which modifies the boundaries of the threshold. The resulting value is processed by an activation function which decides if the input will be transferred to the next neuron.

A CNN usually takes an order 3 tensor as its input, e.g., an image with H rows, W columns, and 3 channels (R, G, B color channels). Higher order tensor inputs, however, can be handled by CNN in a similar fashion. The input then sequentially goes through a series of processing. One processing step is usually called a layer, which could be a convolution layer, a pooling layer, a normalization layer, a fully connected layer, a loss layer, etc. Details to the layers are described in the sections below.

(5)

The above Equation 5 illustrates how a CNN runs layer by layer in a forward pass. The input is $x^1$, usually an image (order 3 tensor). We denote the parameters involved in the first layer's processing collectively as a tensor $w^1$. The output of the first layer is $x^2$, which also acts as the input to the second layer processing. This processing proceeds till all layers in the CNN has been finished, which outputs $x^L$. One additional layer, however, is added for backward error propagation, a method that learns good parameter values in the CNN. Let's suppose the problem at hand is an image classification problem with C classes. A commonly used strategy is to output $x^L$ as a C dimensional vector, whose i-th entry encodes the prediction (posterior probability of $x^1$ comes from the i-th class). To make $x^L$ a probability mass function, we can set the processing in the (L−1)-th layer as a softmax transformation of $x^{L-1}$ (cf. the distance metric and data transformation note). In other applications, the output $x^L$ may have other forms and interpretations. The last layer is a loss layer. Let us suppose t is the corresponding target (ground-truth) value for the input $x^1$, then a cost or loss function can be used to measure the discrepancy between the CNN prediction $x^L$ and the target t. Note that some layers may not have any parameters, that is, $w^i$ may be empty for some i.

In an example of a CNN, ReLu is used as an activation function for the convolutional layers and the softmax activation function provides information in order to give an classification output. The following sections will explain the purpose of the most important layers.

An input image is input to a feature learning section a layer comprising convolution and ReLu, followed by a layer comprising pooling, which is followed by further pairwise repetitions of layers of convolution and ReLu and of pooling. The output of the feature learning section is input to a classification section which comprises layers directed to flattening, fully connecting and softmaxing.

In a convolution layer, multiple convolution kernels are usually used. Assuming D kernels are used and each kernel is of spatial span H×W, we denote all the kernels as f. f is an order 4 tensor in $R^{H \times H \times W \times D^l \times D}$. Similarly, we use index variables $0 \leq i \leq H$, $0 \leq j < W$, $0 \leq d^l < D^l$ and $0 \leq d < D$ to pinpoint a specific element in the kernels. Also note that the set of kernels f refers to the same object as the notation $w^L$ in Equation 5 (seen in chapter Architecture). We change the notation a bit to make the derivation a little bit simpler. It is also clear that even if the mini-batch strategy is used, the kernels remain unchanged.

The spatial extent of the output is smaller than that of the input so long as the convolution kernel is larger than 1×1. Sometimes we need the input and output images to have the same height and width, and a simple padding trick can be used. If the input is $H^l \times W^l \times D^1$ and the kernel size is $H \times W \times D^l \times D$, the convolution result has size $(H^l - H + 1) \times W^l - W + 1) \times D$.

For every channel of the input, if we pad (i.e., insert)

$$\left\lfloor \frac{H-1}{2} \right\rfloor$$

rows above the first row and $$\left\lfloor \frac{H}{2} \right\rfloor$$

rows below the last row, and pad $$\left\lfloor \frac{H-1}{2} \right\rfloor$$

columns to the left of the first column to the left of the first column and $$\left\lfloor \frac{W}{2} \right\rfloor$$

columns to the right of the last column of the input, the convolution output will be $H^l \times W \times D$ in size, i.e., having the same spatial extent as the input. b·c is the floor functions. Elements of the padded rows and columns are usually set to 0, but other values are also possible.

Stride is another important concept in convolution. A kernel is convolved with the input at every possible spatial location, which corresponds to the stride s=1. However, if s>1, every movement of the kernel skip s−1 pixel locations (i.e., the convolution is performed once every s pixels both horizontally and vertically).

In this section, we consider the simple case when the stride is 1 and no padding is used. Hence, we have y (or $x^{l+1}$) in $\mathbb{R}^{H^{l+1} \times W^{l+1} \times D^{l+1}}$, with $H^{l+1}=H^l-H+1$, $W^{l+1}=W^l-W+1$, and $D^{l+1}=D$. In precise mathematics, the convolution procedure can be expressed as an equation:

$$y_{i^{l+1}, j^{l+1}, d} = \sum_{i=0}^{H} \sum_{j=0}^{W} \sum_{d^l=0}^{D^l} f_{i,j,d^l,d} \times x^l_{i^{l+1}+i, j^{l+1}+j, d^l}. \quad (15)$$

Equation 15 is repeated for all $0 \leq d \leq D=D^{l+1}$, and for any spatial location ($i^{l+1}$, $j^{l+1}$) satisfying $0 \leq i^{l+1} < H^l-H+1=H^{l+1}$, $0 \leq j^{l+1} < W^l-W+1=W^{l+1}$. In this equation, $x^l_{i^{l+1}+i, j^{l+1}+j, d^l}$ refers to the element of $x^l$ indexed by the triplet ($i^{l+1}+i, j^{l+1}+j, d^l$). A bias term $b_d$ is usually added to $y_{i^{l+1}, j^{l+1}, d}$. We omit this term in this note for clearer presentation. A pooling function replaces the output of the net at a certain location with a summary statistic of the nearby outputs. For example, a max pooling operation reports the maximum output within a rectangular neighbourhood of a table. Other popular pooling functions include the average of a rectangular neighborhood, the L2 norm of a rectangular neighborhood, or a weighted average based on the distance from the central pixel. In all cases, pooling helps to make the representation approximately invariant to small translations of the input. Invariance to translation means that if we translate the input by a small amount, the values of most of the pooled outputs do not change.

Because pooling summarizes the responses over a whole neighborhood, it is possible to use fewer pooling units than detector units, by reporting summary statistics for pooling regions spaced k pixels apart rather than one pixel apart. This improves the computational efficiency of the network because the next layer has roughly k times fewer inputs to process.

Suppose all the parameters of a CNN model w1, . . . , $w^{L-1}$ have been learned, then we are ready to use this model for prediction. Prediction only involves running the CNN model forward, i.e., in the direction of the arrows in Equation 5 (as seen in the chapter Architecture). Let's take the image classification problem as an example. Starting from the input $x^1$, we make it pass the processing of the first layer (the box with parameters $w^1$), and get $x^2$. In turn, $x^2$ is passed into the second layer, etc. Finally, we achieve $x^l \in \mathbb{R}^C$, which estimates the posterior probabilities of $x^1$ belonging to the C categories. We can output the CNN prediction as $$\arg_i \max x_i^L \quad (2)$$

Now, the problem is: how do we learn the model parameters?

As in many other learning systems, the parameters of a CNN model are optimized to minimize the loss z, i.e., we want the prediction of a CNN model to match the ground-truth labels. Let's suppose one training example $x^1$ is given for training such parameters. The training process involves running the CNN network in both directions. We first run the network in the forward pass to get $x^L$ to achieve a prediction using the current CNN parameters. Instead of outputting a prediction, we need to compare the prediction with the target t corresponding to $x^1$, that is, continue running the forward pass till the last loss layer. Finally, we achieve a loss z. The loss z is then a supervision signal, guiding how the parameters of the model should be modified (updated).

There exist several algorithms for optimizing a loss function and CNNs are not limited to a specific one. An example algorithm is called Stochastic Gradient Descent (SGD). This means the parameters are updated by using the gradient estimated from a (usually) small subset of training examples.

$$w^i \leftarrow w^i - \eta \frac{\delta z}{\delta w^i} \quad (3)$$

In equation 3, the ←—sign implicitly indicates that the parameters $w^i$ (of the i-layer) are updated from time t to t+1. If a time index t is explicitly used, this equation will look like $$(w^i)^{t+1} = (w^i)^t - \eta \frac{\delta z}{\delta (w^i)^t} \quad (4)$$

In equation 3, the partial derivative $$\frac{\delta z}{\delta w^i}$$

measures me rate of increase of z with respect to the changes in different dimensions of $w_i$. This partial derivative vector is called the gradient in mathematical optimization. Hence, in a small local region around the current value of $w^i$, to move $w^i$ in the direction determined by the gradient will increase the objective value z. In order to minimize the loss function, we should update $w^i$ along the opposite direction of the gradient. This updating rule is called the gradient descent.

If we move too far in the negative gradient direction, however, the loss function may increase. Hence, in every update we only change the parameters by a small proportion of the negative gradient, controlled by η (the learning rate). η>0 is usually set to a small number (e.g., η=0.001). One update based on $x^1$ will make the loss smaller for this particular training example if the learning rate is not too large. However, it is very possible that it will make the loss of some other training examples become larger. Hence, we need to update the parameters using all training examples. When all training examples have been used to update the parameters, we say one epoch has been processed. One epoch will in general reduce the average loss on the training set until the learning system overfits the training data. Hence, we can repeat the gradient descent updating epochs and terminate at some point to obtain the CNN parameters (e.g., we can terminate when the average loss on a validation set increases).

The last layer's partial derivatives are easy to compute. Because $x^L$ is connected to z directly under the control of parameters $w^L$, it is easy to compute $$\frac{\delta z}{\delta w^L}.$$

This step is only needed when $w^L$ is not empty. In the same spirit, it is also easy to compute $$\frac{\delta z}{\delta x^L}.$$

For example, if the squared L2 loss is used, we have an empty $$\frac{\delta z}{\delta w^L}, \text{ and } \frac{\delta z}{\delta x^L} = x^L - t.$$

In fact, for every layer, we compute two sets of gradients: the partial derivatives of z with respect to the layer parameters $w^i$, and that layer's input xi. The term $\delta z/\delta w$, as seen in Equation 3, can be used to update the current (i-th) layer's parameters. The term $\delta z/\delta x$, can be used to update parameters backwards, e.g., to the (i−1)-th layer. An intuitive explanation is: $x^i$ is the output of the (i−1)-th layer and $\delta z/\delta x$ is how $x^i$ should be changed to reduce the loss function. Hence, we could view a2, as the part of the "error" supervision information propagated from z backward till the current layer, in a layer by layer fashion. Thus, we can continue the back propagation process, and use $\delta z/\delta x$, to propagate the errors backward to the (i−1)-th layer. This layer-by-layer backward updating procedure makes learning a CNN much easier.

Let's take the i-th layer as an example. When we are updating the i-th layer, the back propagation process for the (i+1)-th layer must have been finished. That is, we already computed the terms $$\frac{\delta z}{\delta w^{i+1}} \text{ and } \frac{\delta z}{\delta x^{i+1}}.$$

Both are stored in memory and ready for use. Now our task is to compute $$\frac{\delta z}{\delta w^i} \text{ and } \frac{\delta z}{\delta x^i}.$$

Using the chain rule, we have $$\frac{\partial z}{\partial (vec(w^i)^T)} = \frac{\partial z}{\partial (vec(x^{i+1})^T)} \frac{\partial vec(x^{i+1})}{\partial (vec(w^i)^T)}.$$

$$\frac{\partial z}{\partial (vec(x^i)^T)} = \frac{\partial z}{\partial (vec(x^{i+1})^T)} \frac{\partial vec(x^{i+1})}{\partial (vec(x^i)^T)}.$$

Since $$\frac{\delta z}{\delta x^{i+1}}$$

is already computed and stored in memory, it requires just a matrix reshaping operation (vec) and an additional transpose operation to get $$\frac{\delta z}{\delta vec(x^{i+1})},$$

which is the first term in the right hand side (RHS) of both equations. So long as we can compute $$\frac{\delta vec(x^{i+1})}{\delta (vec(w^i)^T)} \text{ and } \frac{\delta vec(x^{i+1})}{\delta (vec(x^i)^T)},$$

we can easily get what we want (the left hand side of both equations).

$$\frac{\delta vec(x^{i+1})}{\delta (vec(w^i)^T)} \text{ and } \frac{\delta vec(x^{i+1})}{\delta (vec(x^i)^T)},$$

are much easier to compute than directly computing $$\frac{\delta z}{\delta (vec(w^i)^T)} \text{ and } \frac{\delta z}{\delta (vec(x^i)^T)},$$

because $x^i$ is directly related to $x^{i+1}$, through a function with parameters $w^i$. In the context of neural networks, activation serve as transfer function between the input of a neuron and the output. They define under which conditions the node is activated, i.e. the input values are mapped to the output which, in hidden layers, serves again as one of the inputs to the succeeding neuron. There exist a vast amount of different activation functions with different characteristics.

A loss function quantifies how well an algorithm models the given data. To learn from the data and in order to change the weights from the network, the loss function has to be minimized (see 2.6). Generally, one can make the distinction between a regression loss and classification loss. While in classification, we are trying to predict output from set of finite categorical values (class labels), regression, on the other hand, deals with predicting a continuous value.

In the following mathematical formulations, the following parameters are defined as:

n is the number of training examples i is the i-th training example in a data set $y_i$ is the ground truth label for the i-th training example $\hat{z}_i$ is the prediction for i-th training example The most common setting for classification problems is cross-entropy loss. It increases as the predicted probability diverges from the actual label. The log of the actual predicted probability is multiplied for the ground truth class. An important aspect of this is that cross entropy loss penalizes heavily the predictions that are confident but wrong. The mathematical formulation can be described as:

$$\text{CrossEntropyLoss} = -(y_i \log(\hat{y}_i) + (1-y_i)\log(1 1-\hat{y}_i)) \qquad (5)$$

A typical example for a regression loss is the mean square error or L2 loss. As the name suggests, Mean square error is measured as the average of squared difference between predictions and actual observations. It is only concerned with the average magnitude of error irrespective of their direction. However, due to squaring, predictions which are far away from actual values are penalized heavily in comparison to less deviated predictions. Plus MSE has nice mathematical properties which makes it easier to calculate gradients. Its formulation is as followed:

$$MSE = \frac{1}{n} \cdot \sum_{i=1}^{n} (y_i - \hat{y}_i)^2$$

The following documents contain information on the functioning of convolutional neural networks:

I. Goodfellow, Y. Bengio, and A. Courville, "Deep learning, chapter convolutional networks." http://www.deeplearningbook.org, 2016.

J. Wu, "Introduction to convolutional neural networks." https://pdfs. semanticscholar.org/450c/ a19932fcef1ca6d0442cbf52fec38fb9d1e5.pdf.

"Common loss functions in machine learning." https:// towardsdatascience.com/common-loss-functions-in-machine-learning-46af0ffc4d23. Accessed: Aug. 22, 2019.

Alex Krizhevsky, Ilya Sutskever, and Geoffrey E. Hinton, "Imagenet classification with deep convolutional neural networks." http://papers.nips.cc/paper/4824-imagenet-classification-with-deep-convolutional-neural-networks. pdf S. Ren, K. He, R. Girshick, and J. Sun, "Faster r-cnn: Towards real-time object detection with region proposal networks." https://arxiv.org/pdf/1506.01497.pdf.

S.-E. Wei, V. Ramakrishna, T. Kanade, and Y. Sheikh, "Convolutional pose machines." https://arxiv.org/pdf/ 1602.00134.pdf.

Jonathan Long, Evan Shelhamer, and Trevor Darrell, "Fully convolutional networks for semantic segmentation." https://www.cv-foundation.org/openaccess/content_cvpr_2015/papers/Long_Fully_Convolutional_Networks_2015_ CVPR_paper.pdf.

The invention claimed is:

1. A computer-implemented method of training a machine learning model for determining position of an image representation of an annotated anatomical structure in a two-dimensional x-ray image, the method comprising the following steps:
   acquiring atlas data which describes a three-dimensional shape of the anatomical structure and at least one projection parameter for generating two-dimensional x-ray images of the anatomical structure;
   acquiring image training data which describes the two-dimensional x-ray images being digitally reconstructed radiographs and including an image representation of the anatomical structure, wherein the two-dimensional x-ray images are generated based on the at least one projection parameter that is described in the atlas data for the anatomical structure;
   acquiring annotation data which describes an annotation for the anatomical structure; and
   determining model parameter data which describes model parameters of the machine learning model for establishing a relation between the anatomical structure in the two-dimensional x-ray images and the annotation, wherein the model parameter data is determined by training the model parameter data through inputting the image training data and the annotation data into a function which establishes the relation, the function being part of the machine learning model.

2. The method according to claim 1, wherein
   the atlas data describes an image-based model of the anatomical structure, and
   the annotation data is determined based on the image training data and the atlas data.

3. The method according to claim 1, wherein the annotation data is determined from metadata included in the image training data.

4. The method according to claim 1, wherein the function establishes a relation between a position of the anatomical structure in the two-dimensional x-ray images and a position for displaying the annotation in the two-dimensional x-ray images.

5. The method according to claim 1, comprising the following steps:
   acquiring medical image data which describes three-dimensional medical images including an image representation of the anatomical structure,
   wherein the image training data is determined by
      determining an image value threshold associated with the image representation of the anatomical structure in the three-dimensional medical images and
      defining a corresponding intensity mapping function and generating the image representation of the anatomical structure in each of the synthesized two-dimensional x-ray images from the image representation of the anatomical structure in one of the three-dimensional medical images based on the intensity mapping function.

6. The method according to claim 1, wherein the machine learning model comprises a machine learning algorithm.

7. The method according to claim 1, wherein a convolutional neural network is part of the machine learning model.

8. The method according to claim 1, wherein the model parameters define learnable parameters of the machine learning model.

9. A computer-implemented method of determining a relation between an anatomical structure represented in a two-dimensional medical image and an annotation for the anatomical structure, the method comprising:
   acquiring patient image data which describes a two-dimensional x-ray image including an image representation of the anatomical structure of a patient; and
   determining structure annotation prediction data which describes, according to a certain likelihood determined by a trained machine learning model, a position of the image representation of the anatomical structure in the two-dimensional x-ray image described by the patient image data and the annotation for the anatomical structure,
   wherein the structure annotation prediction data is determined by inputting the patient image data into a function which establishes a relation between the image representation of the anatomical structure in the two-dimensional x-ray image and the annotation for the anatomical structure, the function being part of the trained machine learning model, and
   wherein the machine learning model is trained using two-dimensional x-ray images generated based on a projection parameter described in atlas data for the anatomical structure, the atlas data describing a three-dimensional shape of the anatomical structure.

10. The method according to claim 9, wherein the patient image data has been generated by synthesizing the two-dimensional x-ray image from a three-dimensional image of the anatomical structure, or wherein the patient image data has been generated by applying a fluoroscopic imaging modality to the anatomical structure.

11. The method according to claim 9, wherein the function establishes a relation between a position of the anatomical structure in the two-dimensional x-ray image described by the patient image data and a position for displaying the annotation in the two-dimensional x-ray image described by the patient image data, and wherein the structure annotation prediction data describes a relation between the position of the image representation of the anatomical structure in the two-dimensional x-ray image described by the patient image data and a position for displaying the annotation for the anatomical structure in the two-dimensional x-ray image described by the patient image data.

12. A system for determining a relation between an anatomical structure represented in a two-dimensional medical image and an annotation for the anatomical structure, comprising:
   at least one computer having memory with instructions stored thereon operable to:
      acquire patient image data which describes a two-dimensional x-ray image including an image representation of an anatomical structure of a patient; and
      determine structure annotation prediction data which describes, according to a certain likelihood determined by a machine learning model, a position of the image representation of the anatomical structure in the two-dimensional x-ray image described by the patient image data and an annotation for the anatomical structure,
      wherein the structure annotation prediction data is determined by inputting the patient image data into a function which establishes a relation between the image representation of the anatomical structure in the two-dimensional x-ray image and the annotation for the anatomical structure, the function being part of the machine learning model, and
      wherein the machine learning model is trained using two-dimensional x-ray images generated based on a projection parameter described in atlas data for the anatomical structure, the atlas data describing a three-dimensional shape of the anatomical structure;
   at least one electronic data storage device storing the patient image data;
   wherein the at least one computer is operably coupled to
      the at least one electronic data storage device for acquiring, from the at least one electronic data storage device, the patient image data, and for storing, in the at least one electronic data storage device, at least the structure annotation prediction data; and
   program storage medium for acquiring, the data defining model parameters of the machine learning model.

13. A non-transitory computer storage medium comprising instructions for determining a relation between an anatomical structure represented in a two-dimensional medical image and an annotation for the anatomical structure, the instructions operable to cause at least one processor to:
   acquire patient image data which describes a two-dimensional x-ray image including an image representation of an anatomical structure of a patient; and
   determine structure annotation prediction data which describes, according to a certain likelihood determined by a machine learning model, a position of the image representation of the anatomical structure in the two-dimensional x-ray image described by the patient image data and an annotation for the anatomical structure,
      wherein the structure annotation prediction data is determined by inputting the patient image data into a function which establishes a relation between the image representation of the anatomical structure in the two-dimensional x-ray image and the annotation for the anatomical structure, the function being part of the machine learning model, and
      wherein the machine learning model is trained using two-dimensional x-ray images generated based on a projection parameter described in atlas data for the anatomical structure, the atlas data describing a three-dimensional shape of the anatomical structure.

* * * * *

UNITED STATES PATENT AND TRADEMARK OFFICE
CERTIFICATE OF CORRECTION

PATENT NO. : 12,080,021 B2
APPLICATION NO. : 17/274580
DATED : September 3, 2024
INVENTOR(S) : Kim Le et al.

It is certified that error appears in the above-identified patent and that said Letters Patent is hereby corrected as shown below:

In the Specification

In Column 15, Line 25, delete "($x_i$, ..., $x_n$)" and insert -- $(x_1, ..., x_n)$ --, therefor.

In Column 15, Line 33, delete " $z = \sum_{i=0}^{m} x_i \cdot w_i$ " and insert -- $z = \sum_{i=0}^{n} x_i \cdot w_i$ --, therefor.

In Column 16, Line 31, delete "$R^{H \times H \times W \times D' \times D}$." and insert -- $\mathbb{R}^{H \times W \times D' \times D}$ --, therefor.

In Column 17, Line 6, delete "$H^l \times W \times D$" and insert -- $H^l \times W^l \times D$ --, therefor.

In Column 18, Line 44, delete "me" and insert -- the --, therefor.

In Column 18, Line 45, delete "$w_i$." and insert -- $w^j$. --, therefor.

In Column 19, Line 34, delete "a2," and insert -- $\frac{\delta z}{\delta x^i}$ --, therefor.

In Column 20, Line 62, delete "$\hat{2}_i$," and insert -- $\hat{y}_i$ --, therefor.

In Column 21, Line 3, delete "CrossEntropyLoss=−($y_i$ log($\hat{y}_i$)+(1−$y_i$)log(11-$\hat{y}_i$))" and insert -- $CrossEntropyLoss = -(y_i log(\hat{y}_i) + (1 - y_i)log(1 - \hat{y}_i))$ --, therefor.

Signed and Sealed this
Fifth Day of November, 2024

Katherine Kelly Vidal
*Director of the United States Patent and Trademark Office*